United States Patent
Lee et al.

(10) Patent No.: US 11,685,939 B2
(45) Date of Patent: Jun. 27, 2023

(54) **METHOD FOR PRODUCING CIS-UNSATURATED FATTY ACID BY RECOMBINANT *CANDIDA RUGOSA* LIPASE 1 (RCRL1)**

(71) Applicants: CHANT OIL CO., LTD., New Taipei (TW); National Taiwan Normal University, Taipei (TW)

(72) Inventors: Guan-Chiun Lee, Taipei (TW); Ting-Chun Kuo, New Taipei (TW); Shun-Niang Chen, Yilan County (TW); Chia-Chi Lin, Hsinchu (TW)

(73) Assignees: CHANT OIL CO., LTD., New Taipei (TW); National Taiwan Normal University, Taipei (TW)

( * ) Notice: Subject to any disclaimer, the term of this patent is extended or adjusted under 35 U.S.C. 154(b) by 135 days.

(21) Appl. No.: 17/230,155

(22) Filed: Apr. 14, 2021

(65) Prior Publication Data

US 2022/0098628 A1 Mar. 31, 2022

(30) Foreign Application Priority Data

Sep. 30, 2020 (TW) ................................. 109134294

(51) Int. Cl.
| | | |
|---|---|---|
| *C12P 7/6418* | (2022.01) | |
| *C12N 9/20* | (2006.01) | |
| *C12P 7/6409* | (2022.01) | |
| *C12P 7/6463* | (2022.01) | |
| *C12R 1/72* | (2006.01) | |

(52) U.S. Cl.
CPC ........ *C12P 7/6463* (2013.01); *C12R 2001/72* (2021.05)

(58) Field of Classification Search
CPC .. C12P 7/6463; C12P 7/6418; C12R 2001/72; C12N 9/20
See application file for complete search history.

(56) References Cited

FOREIGN PATENT DOCUMENTS

| CA | 2163815 A1 * | 5/1996 | ................ C12P 7/64 |
|---|---|---|---|
| CN | 1470627 A | 1/2004 | |
| CN | 101294170 B | 12/2011 | |

OTHER PUBLICATIONS

Chang, S-W. et al., "Codon Optimization of *Candida rugosa* lip1 Gene for Improving Expression in Pichia pastoris and Biochemical Characterization of the Purified Recombinant LIP1 Lipase", J. Agric. Food Chem., 54, 2006, 815-822.

De Renobales, M. et al., "Hydrolysis of Animall Fats by Lipase at Temperatures Below Their Melting Points", Bio. Let., vol. 14, No. 8, Aug. 1992, 683-688.

* cited by examiner

*Primary Examiner* — Satyendra K Singh
(74) *Attorney, Agent, or Firm* — Joseph C. Zucchero; Carolyn S. Elmore; Elmore Patent Law Group, P.C.

(57) ABSTRACT

A method for producing cis-unsaturated fatty acid includes the operations below. (i) An oil-water mixture is provided, wherein the oil-water mixture includes 1 to 10 parts by weight of oil and 1 part by weight of water. (ii) 0.002 to 0.5 parts by weight of a recombinant *Candida rugosa* lipase 1 (rCRL1) is added into the oil-water mixture. (iii) The oil-water mixture is emulsified. (iv) The emulsified oil-water mixture is hydrolyzed and fatty acid is generated. (v) Oil-water is separated at a temperature of 55° C. to 65° C. and an oil phase layer is extracted. (vi) The cooling and filtering step is performed to obtain cis-unsaturated fatty acid.

13 Claims, 8 Drawing Sheets

METHOD FOR PRODUCING CIS-UNSATURATED FATTY ACID BY RECOMBINANT *CANDIDA RUGOSA* LIPASE 1 (RCRL1)

CROSS-REFERENCE TO RELATED APPLICATION

This application claims priority to Taiwan Application Serial Number 109134294, filed Sep. 30, 2020, which is herein incorporated by reference in its entirety.

BACKGROUND

Field of Invention

The present invention relates to a method for producing cis-unsaturated fatty acid by recombinant *Candida rugosa* lipase 1 (rCRL1).

Description of Related Art

Generally speaking, industrial production of edible oil is from natural oils and production of fatty acids from hydrolyzing natural oils. These processes usually undergo high-temperature and high-pressure treatment (for example, the high-temperature is about 210-265° C., and the high-pressure is about 2-7 MPa), which in turn leads to the conversion of cis-unsaturated fatty acids in natural oils into trans-unsaturated fatty acids, so that the products contain a large amount of trans-unsaturated fatty acids. Studies have shown that, compared to trans-unsaturated fatty acids, cis-unsaturated fatty acids are less likely to cause cardiovascular disease in the human body. The use of enzymes for low-temperature hydrolysis can avoid the production of trans-unsaturated fatty acids, retain the nutrients in natural oils, and save equipment costs and energy.

The versatile *Candida rugosa* lipase (CRL) has been widely used in biotechnological applications. However, most applications in hydrolyzing triglycerides to produce fatty acids are carried out using commercial CRL preparations, i.e. a mixture of various isoenzymes (CRL1-5). It is currently known that CRL1 is the lipase with the best hydrolysis efficiency among all isozymes. Because different isoenzymes have different catalytic properties, there are often problems of non-reproducible enzymatic reaction. Moreover, the types of enzymes used are mostly immobilized forms, and organic solvents are often added to the enzyme reaction to help dissolve oils, so there are disadvantages such as high enzyme cost, complex production processes, and environmental-unfriendly.

SUMMARY

In view of this, the lipase used in the present disclosure is a single type of recombinant *Candida rugosa* lipase (rCRL1) for low-temperature hydrolysis, and the use of a single type of enzyme has the advantage of stable quality. The previous research (J Agric Food Chem. 2006 Feb. 8; 54(3):815-22) has not been applied to the hydrolysis of fats as well as in mass production. Therefore, the present invention is aimed at fermenting and mass production of this enzyme and directly using the fermentation broth for the hydrolysis reaction, further reducing the production cost.

One aspect of the present disclosure provides a method for producing cis-unsaturated fatty acid by recombinant *Candida rugosa* lipase 1 (rCRL1). The method includes the following operations: (i) providing an oil-water mixture, in which the oil-water mixture includes 1 to 10 parts by weight of oil and 1 part by weight of water; (ii) adding 0.002 to 0.5 parts by weight of a recombinant *Candida rugosa* lipase 1 (rCRL1) into the oil-water mixture; (iii) after operation (ii), emulsifying the oil-water mixture; (iv) after operation (iii), hydrolyzing the emulsified oil-water mixture to generate fatty acid; (v) after operation (iv), performing an oil-water separation at a temperature of 55° C. to 65° C. and extracting an oil phase layer; and (vi) after operation (v), performing a cooling and filtering step to obtain cis-unsaturated fatty acid.

In some embodiments of the present disclosure, the oil includes a natural woody vegetable oil, a natural herbal oil, a natural animal oil, and a combination thereof.

In some embodiments of the present disclosure, the natural woody vegetable oil includes palm oil, palm kernel oil, olive oil, and camellia oil.

In some embodiments of the present disclosure, the natural herbal oil includes soybean oil, rapeseed oil, peanut oil, sesame oil, and sunflower oil.

In some embodiments of the present disclosure, the natural animal oil includes tallow, lard, and fish oil.

In some embodiments of the present disclosure, the operation (iii) is carried out at a temperature from about 25° C. to about 40° C.

In some embodiments of the present disclosure, the operation (iv) is carried out at a temperature from about 25° C. to about 40° C.

In some embodiments of the present disclosure, the operation (iii) is carried out for about 1-6 hours.

In some embodiments of the present disclosure, the operation (iv) is carried out for about 10-40 hours.

In some embodiments of the present disclosure, the foregoing cooling and filtering step is multiple continuous cooling and filtering steps. The multiple continuous cooling and filtering steps includes a first cooling and filtering step, a second cooling and filtering step, a third cooling and filtering step, and a fourth cooling and filtering step. A first cooling temperature drops from about 55-65° C. to about 45-48° C. A second cooling temperature drops from about 45-48° C. to about 34-37° C. A third cooling temperature drops from about 34-37° C. to about 23-27° C. A fourth cooling temperature drops from about 23-27° C. to about 16-19° C.

In some embodiments of the present disclosure, the foregoing cooling and filtering step is a single cooling and filtering step, and a cooling temperature drops from about 55-65° C. to about 16-19° C.

In some embodiments of the present disclosure, the oil-water mixture includes 1 to 2 parts by weight of oil and 1 part by weight of water.

In some embodiments of the present disclosure, 0.02 to 0.25 parts by weight of the recombinant *Candida rugosa* lipase 1 (rCRL1) is added into the oil-water mixture.

In some embodiments of the present disclosure, the oil-water mixture is emulsified by a stirring way.

In some embodiments of the present disclosure, a stirring speed ranges from about 250 rpm to about 500 rpm.

BRIEF DESCRIPTION OF THE DRAWINGS

The invention can be more fully understood by reading the following detailed description of the embodiment, with reference made to the accompanying drawings as follows.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. The embodiments disclosed below may be combined or substituted with each other under beneficial circumstances, and other embodiments may also be added to an embodiment without further description.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "lipase" (also known as glyceride hydrolase) is a type of carboxyl ester hydrolase. Lipase can hydrolyze fat (triglyceride) into glycerol and fatty acid under natural conditions.

"*Candida rugosa* lipase (CRL)" refers to the *Candida rugosa* lipase isozyme, which includes the natural *Candida rugosa* lipase or its variants (hereinafter also referred to as recombinant *Candida rugosa* lipase). For example, *Candida rugosa* produces at least five diverse lipases, and the amino acid sequences of these five lipases are highly similar, but they have different substrate specificities. "Isozymes" refers to enzymes with different properties but the same catalytic reaction, which can be present in different tissues or organs of an organism in different amounts. These differences can be reflected in the primary structure of the protein, or in the quaternary structure or post-translational modification. Isozymes can be used by cells to regulate enzyme activity according to specific physiological conditions in the cell.

Figure 1:
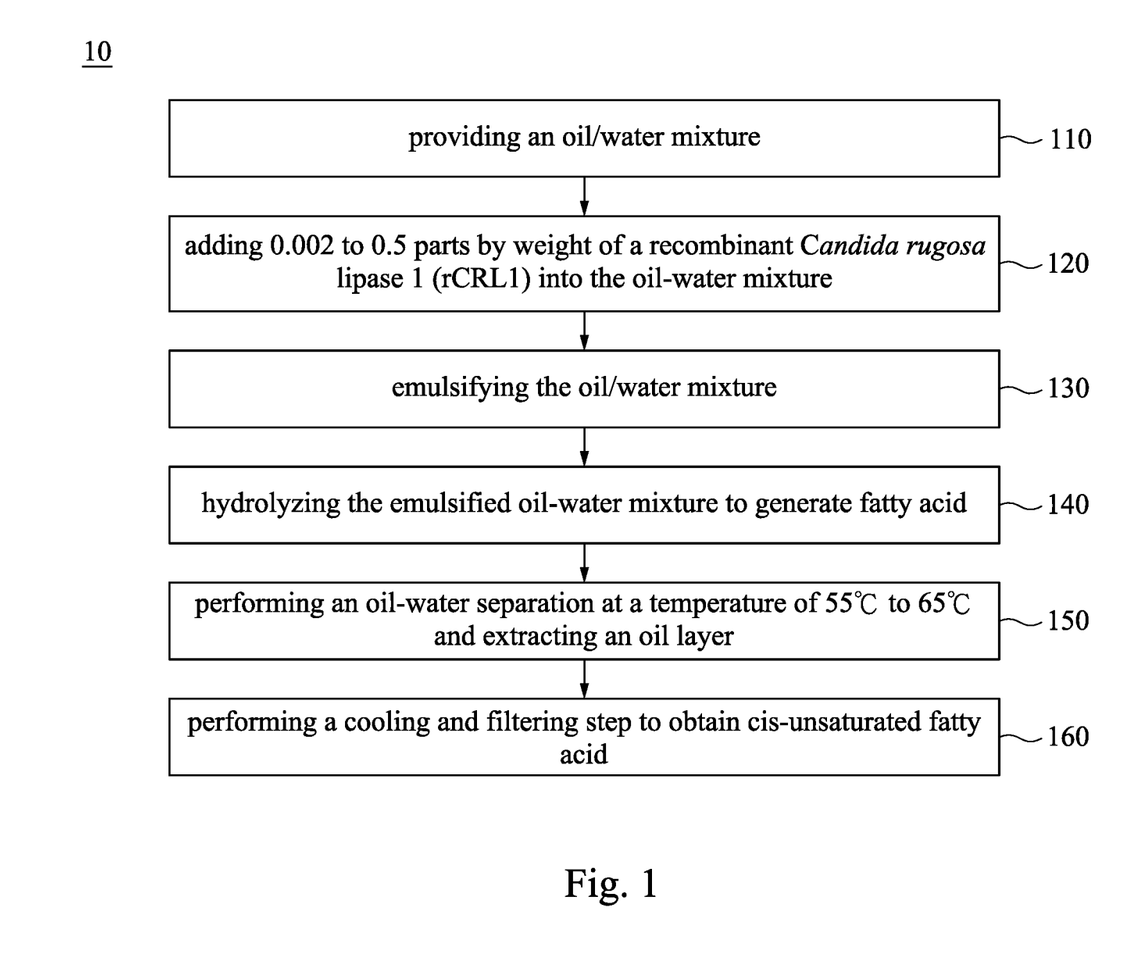
FIG. 1 is a flow chart of a method for producing cis-unsaturated fatty acid by recombinant *Candida rugosa* lipase according to some embodiments of the present disclosure.

One aspect of the present disclosure provides a method for producing cis-unsaturated fatty acid by recombinant *Candida rugosa* lipase. FIG. 1 is a flow chart of a method 10 for producing cis-unsaturated fatty acid by recombinant *Candida rugosa* lipase according to some embodiments of the present disclosure. As shown in FIG. 1, the method 10 for producing cis-unsaturated fatty acid at least includes operation 110, operation 120, operation 130, operation 140, operation 150, and operation 160.

In operation 110, an oil-water mixture is provided. To be specific, the oil-water mixture includes 1 to 10 parts by weight of oil and 1 part by weight of water. In various embodiments, the oil includes a natural woody vegetable oil, a natural herbal oil, a natural animal oil, and a combination thereof. In some embodiments, the natural woody vegetable oil includes palm oils, palm kernel oils, olive oils, and camellia oils, but not limited thereto. In some embodiments, the natural herbal oil includes soybean oils, rape-seed oils, groundnut oils, sesame oils, and sunflower-seed oils, but not limited thereto. In some embodiments, the natural animal oil includes beef tallow, lard, and fish oils. In this embodiment, the choice of oil is preferably natural woody vegetable oils, natural herbal oils, and natural animal oils.

In some embodiments, the oil-water mixture includes 1 part by weight of oil and 1 part by weight of water. In some embodiments, the oil-water mixture includes 2 parts by weight of oil and 1 part by weight of water. In some embodiments, the oil-water mixture includes 3 parts by weight of oil and 1 part by weight of water. In some embodiments, the oil-water mixture includes 4 parts by weight of oil and 1 part by weight of water. In some embodiments, the oil-water mixture includes 5 parts by weight of oil and 1 part by weight of water. In some embodiments, the oil-water mixture includes 6 parts by weight of oil and 1 part by weight of water. In some embodiments, the oil-water mixture includes 7 parts by weight of oil and 1 part by weight of water. In some embodiments, the oil-water mixture includes 8 parts by weight of oil and 1 part by weight of water. In some embodiments, the oil-water mixture includes 9 parts by weight of oil and 1 part by weight of water. In some embodiments, the oil-water mixture includes 10 parts by weight of oil and 1 part by weight of water.

In operation 120, 0.002 to 0.5 parts by weight of a recombinant *Candida rugosa* lipase 1 (rCRL1) is added into the above oil-water mixture. In some embodiments, 0.003 parts by weight of rCRL1, 0.005 parts by weight of rCRL1, 0.007 parts by weight of rCRL1, 0.009 parts by weight of rCRL1, 0.01 parts by weight of rCRL1, 0.03 parts by weight of rCRL1, 0.05 parts by weight of rCRL1, 0.07 parts by weight of rCRL1, 0.09 parts by weight of rCRL1, 0.1 parts by weight of rCRL1, 0.15 parts by weight of rCRL1, 0.2 parts by weight of rCRL1, 0.25 parts by weight of rCRL1, 0.3 parts by weight of rCRL1, 0.35 parts by weight of rCRL1, 0.4 parts by weight of rCRL1, 0.45 parts by weight of rCRL1, or 0.5 parts by weight of rCRL1 can be added into the above-mentioned oil-water mixture.

The recombinant *Candida rugosa* lipase used in the present disclosure is rCRL1. The detailed amino acid sequence and properties of rCRL1 can refer to the following reference: Codon optimization of *Candida rugosa* lip1 gene for improving expression in *Pichia pastoris* and biochemical characterization of the purified recombinant LIP1 lipase (J Agric Food Chem. 2006 Feb. 8; 54(3):815-22). More specifically, the recombinant *Candida rugosa* lipase (rCRL1) is a yeast fermentation broth. The enzyme activity of the unconcentrated fermentation broth is 1600 U/mL. For example, olive oil emulsified with polyvinyl alcohol is used as substrate for activity analysis. It is noted that the unit 1 U corresponds to the amount of enzyme that releases 1 μmol of fatty acid per minute at 37° C.

In operation 130, the oil-water mixture is emulsified after operation 120. In some embodiments, the oil-water mixture may be emulsified by stirring. For example, the stirring speed may be about 250 rpm to about 500 rpm, such as 300 rpm. In some embodiments, the emulsification is carried out at a temperature of about 25-40° C. In some embodiments, the emulsification may be carried out at about 27° C., about 29° C., about 30° C., about 31° C., about 33° C., about 35° C., about 37° C., or about 39° C.

In operation 140, the emulsified oil-water mixture is subjected to a hydrolysis reaction to generate fatty acid after operation 130. In some embodiments, the hydrolysis reaction is carried out at a temperature of about 25-40° C. In various embodiments, the hydrolysis reaction may be carried out at about 27° C., about 29° C., about 30° C., about 31° C., about 33° C., about 35° C., about 37° C., or about 39° C. In some embodiments, the hydrolysis reaction lasts for about 10-40 hours, such as about 12 hours, about 14 hours, about 16 hours, about 18 hours, about 20 hours, about 22 hours, about 24 hours, about 26 hours, about 28 hours, about 30 hours, about 32 hours, about 34 hours, about 36 hours, about 38 hours, or about 40 hours. The hydrolysis reaction time depends on the amount of the oil-water mixture. In some embodiments, after operation 130, the emulsified oil-water mixture is allowed to stand still without stirring, so that a higher hydrolysis reaction rate can be achieved.

In operation 150, after operation 140, an oil-water separation is performed at a temperature of about 55-65° C., and an oil phase layer is extracted. To be specific, the separation of the fatty acid in oil phase layer may be performed at a temperature of about 55-65° C., and the oil phase layer is extracted. In some embodiments, the oil-water separation may be performed at a temperature of about 57° C., about 59° C., about 60° C., about 61° C., or about 63° C.

In operation 160, a cooling and filtering step for the oil phase layer is performed after operation 150. In some embodiments, the operation 160 may be performing multiple continuous cooling and filtering steps to the oil phase layer, and the multiple continuous cooling and filtering steps include four continuous cooling and filtering steps. For example, a temperature of the first cooling and filtering step drops from about 55-65° C. to about 45-48° C., a temperature of the second cooling and filtering step drops from about 45-48° C. to about 34-37° C., a temperature of the third cooling and filtering step drops from about 34-37° C. to about 23-27° C., and a temperature of the fourth cooling and filtering step drops from about 23-27° C. to about 16-19° C.

In another embodiment, the operation 160 may be to perform a single cooling and filtering step, and a cooling temperature drops from about 55-65° C. to about 16-19° C.

The method for producing cis-unsaturated fatty acids disclosed in the present disclosure uses a single CRL isozyme (i.e., rCRL1) to hydrolysis fats and oil. After emulsification in an oil-water two-phase system without adding organic solvents, and then standing or stirring, the rCRL1 in the water phase may continue to hydrolyze the oil and free fatty acids are obtained. Moreover, after the hydrolysis oil phase is slowly cooled and filtered, the content of cis-unsaturated fatty acids in the filtrate can reach more than about 75%. In addition, since the operating temperatures of the both standing process and filtering process do not exceed 100° C., the cis-unsaturated fatty acids in the filtrate will not be converted into trans-unsaturated fatty acids, thereby retaining most of the cis-unsaturated fatty acids that are originally present in the oil.

The following Examples are provided to illustrate certain aspects of the present disclosure and to aid those of skill in the art in practicing this disclosure. These Examples are in no way to be considered to limit the scope of the disclosure in any manner.

As used below, the term "acid value (AV)" is measured using the National Standards of the Republic of China (CNS) 3647-N6082 in the Method of test for edible oils and fats—Determination of acid value. The term "saponification value (SV)" is measured using the National Standards of the Republic of China (CNS) 3468-N6083 in the Method of test for edible oils and fats—Determination of saponification value. The term "iodine value (IV)" is measured using the National Standards of the Republic of China (CNS) 15060-K61136 in the Biodiesel—Fatty acid methyl ester (FAME)—Determination of iodine value.

Experimental Example 1 Hydrolysis of Crude Palm Oil

In this experimental example, an oil-water mixture of crude palm oil and water in the same oil-water ratio was used. The same concentration of rCRL1 was used. Under the above conditions, the oil-water mixture was stirred and emulsified at different temperatures (about 30° C. and about 37° C.), and a hydrolysis reaction was carried out for about 2-4 hours. Next, after solidified fatty acid crystals were produced in the samples, the samples were allowed to stand. The acid value (AV) and the hydrolysis rate (%) in an oil phase layer of the samples were sampled and analyzed at regular period of time. The results are listed in table 1 below.

TABLE 1

| Hydrolysis reaction time (hr) | Example 1 | | Example 2 | |
|---|---|---|---|---|
| | Oil:water (g:g) | | | |
| | 500:250 | | 500:250 | |
| | Amount of rCRL1 (g) | | | |
| | 15 | | 15 | |
| | temperature | | | |
| | 37° C. | | 30° C. | |
| | Reaction method | | | |
| | standing after emulsification | | standing after emulsification | |
| | AV | Hydrolysis rate (%) | AV | Hydrolysis rate (%) |
| 0 | 12.7 | 6.4 | 12.7 | 6.4 |
| 2 | 90.9 | 45.6 | 121.2 | 60.8 |
| 4 | 154.7 | 77.7 | 171.3 | 86.0 |
| 6 | 181.5 | 91.1 | 187.3 | 94.0 |
| 8 | 187.5 | 94.1 | 191.6 | 96.2 |
| 10 | 192.0 | 96.4 | 195.7 | 98.2 |
| 12 | 192.9 | 96.8 | 196.1 | 98.4 |
| 14 | 193.5 | 97.1 | 196.0 | 98.4 |
| 16 | 192.8 | 96.8 | 196.1 | 98.4 |
| 18 | 193.6 | 97.2 | 196.8 | 98.8 |

It can be seen from table 1 that the AV measured in the oil phase layer of example 1 was about 193.6 and the hydrolysis rate was about 97.2%. The AV measured in the oil phase layer of example 2 was about 196.8 and the hydrolysis rate was about 98.8%. It means that the hydrolysis rate of example 2 is higher than that of example 1. It is noted that the hydrolysis rate is calculated by dividing the AV in the oil phase layer by the saponification value (SV).

Figure 2:
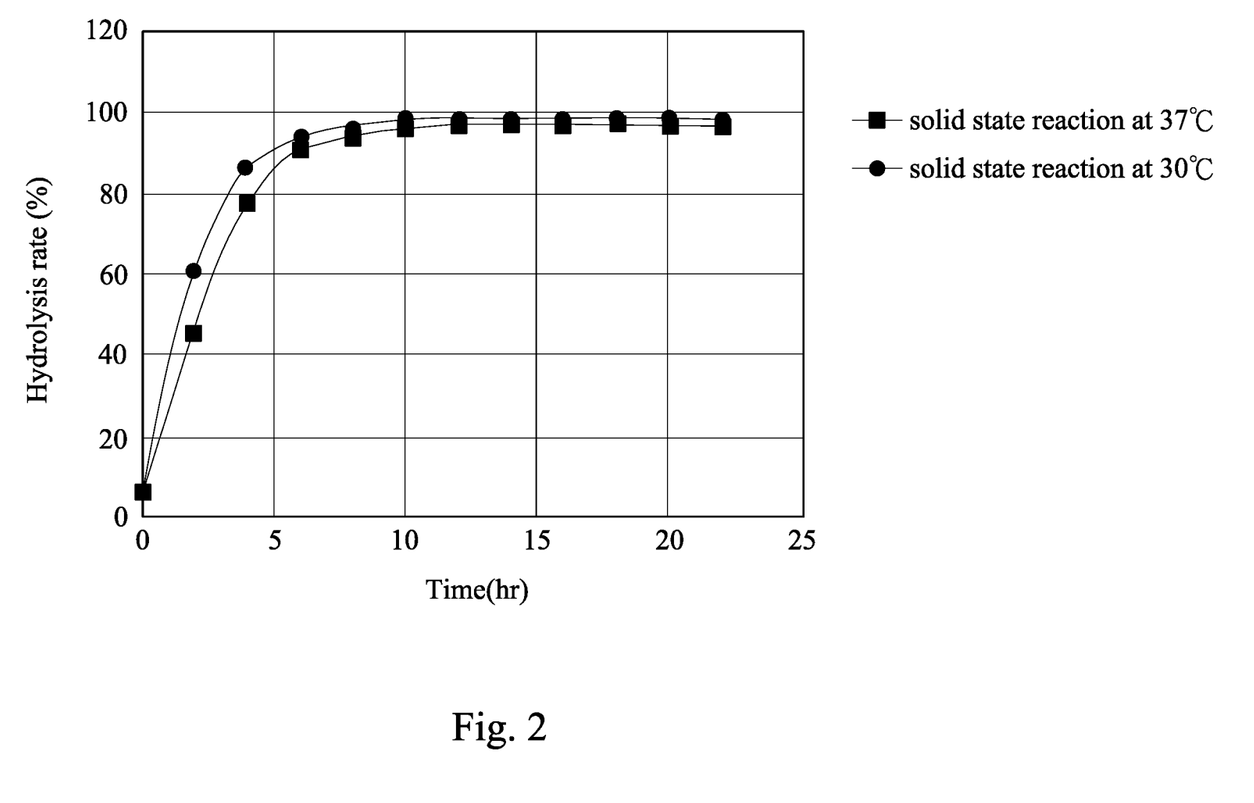
FIG. 2 is a hydrolysis rate relationship diagram of hydrolyzed crude palm oil at different temperatures after emulsification and hydrolysis reactions according to some embodiments of the present disclosure.

FIG. 2 is a hydrolysis rate relationship diagram of hydrolyzed crude palm oil at different temperatures after emulsification and hydrolysis reactions according to some embodiments of the present disclosure. Referring to FIG. 2, the results of example 1 and example 2 were integrated in FIG. 2 to compare the hydrolysis rate under different reaction conditions.

Experimental Example 2 Hydrolysis of Tallow

In this experimental example, an oil-water mixture of tallow and water in different oil-water ratio was used. The same concentration of rCRL1 was used. Under the above conditions, the oil-water mixture was stirred and emulsified at different temperatures (about 30° C. and about 37° C.) and a hydrolysis reaction was carried out. At the beginning of this reaction, solidified fatty acid crystals were produced and then stood for hydrolysis. The acid value (AV) and the hydrolysis rate (%) in an oil phase layer of the samples were sampled and analyzed at regular period of time. The results are listed in table 2 below.

TABLE 2

| | Example 3 | | Example 4 | | Example 5 | | Example 6 | |
|---|---|---|---|---|---|---|---|---|
| Oil:water (g:g) | | | | | | | | |
| | 200:100 | | 200:100 | | 200:200 | | 200:200 | |
| Amount of rCRL1 (g) | | | | | | | | |
| | 10 | | 10 | | 10 | | 10 | |
| temperature | | | | | | | | |
| | 37° C. | | 30° C. | | 37° C. | | 30° C. | |
| Reaction method | | | | | | | | |
| | standing after emulsification | | standing after emulsification | | standing after emulsification | | standing after emulsification | |
| Time (hr) | AV | Hydrolysis rate (%) | AV | Hydrolysis rate (%) | AV | Hydrolysis rate (%) | AV | Hydrolysis rate (%) |
| 0 | 6 | 3.0 | 6 | 3.0 | 6 | 3.0 | 6 | 3.0 |
| 2 | 119 | 60.1 | 102.8 | 51.9 | 121.2 | 61.2 | 99.4 | 50.2 |
| 4 | 142.6 | 72.1 | 132.9 | 67.2 | 142.7 | 72.1 | 129.2 | 65.3 |
| 6 | 151.4 | 76.5 | 150.2 | 75.9 | 152.2 | 76.9 | 146 | 73.8 |
| 8 | 157.9 | 79.8 | 159.3 | 80.5 | 158.6 | 80.1 | 157.9 | 79.8 |
| 12 | 165.9 | 83.8 | 168.8 | 85.3 | 167.8 | 84.8 | 170.6 | 86.2 |
| 16 | 172.3 | 87.1 | 173.8 | 87.8 | 176.2 | 89.0 | 175.1 | 88.5 |
| 20 | 178.8 | 90.3 | 180.3 | 91.1 | 178.5 | 90.2 | 179.8 | 90.9 |
| 28 | 182 | 92.0 | 183.2 | 92.6 | 184.5 | 93.2 | 185.1 | 93.5 |
| 36 | 183.5 | 92.7 | 184.8 | 93.4 | 184.9 | 93.4 | 188.3 | 95.1 |
| 40 | 184.7 | 93.3 | 185.5 | 93.7 | 186.9 | 94.4 | 189.2 | 95.6 |

It can be seen from table 2 that since tallow is a high melting point fat, the high melting point free fatty acid produced after hydrolysis reaction may immediately produce solidified fatty acid crystals at a lower temperature, which facilitates the continuous progress of the hydrolysis reaction. In the embodiment of oil-water ratio being 2:1, the hydrolysis rate of example 4 (the hydrolysis reaction temperature of about 30° C.) was better than that of example 3 (the hydrolysis reaction temperature of about 37° C.). In the embodiment of oil-water ratio being 1:1, the hydrolysis rate of example 6 (the hydrolysis reaction temperature of about 30° C.) was better than that of example 5 (the hydrolysis reaction temperature of about 37° C.).

Compared with example 4, in the hydrolysis reaction time of about 40 hours, the AV measured in the oil phase layer of example 6 was about 189.2 and the hydrolysis rate was about 95.6%. It means that when the oil-water ratio in the oil-water mixture was changed from 2:1 to 1:1, the hydrolysis rate and reaction rate could be significantly improved.

The literature "Hydrolysis of Animal Fats By Lipase at Temperature Below There Melting Points (Biotechnology Letters, 1992 Aug. 14(8):683-688)" pointed out that the commercial mixed *Candida rugosa* lipase (Meito Sangyo) is used to hydrolyze tallow, in which the oil-water ratio was 1:1, and the amount of enzyme was 180 U per gram tallow, and the hydrolysis rate could reach 93.7% after hydrolyzing at 30° C. for 24 hours. This result is similar to example 6. However, the amount of rCRL1 in example 6 was about 80 U per gram tallow, which was less than the amount of commercial enzymes. Example 6 has the advantage of reducing the cost of enzymes.

Figure 3:
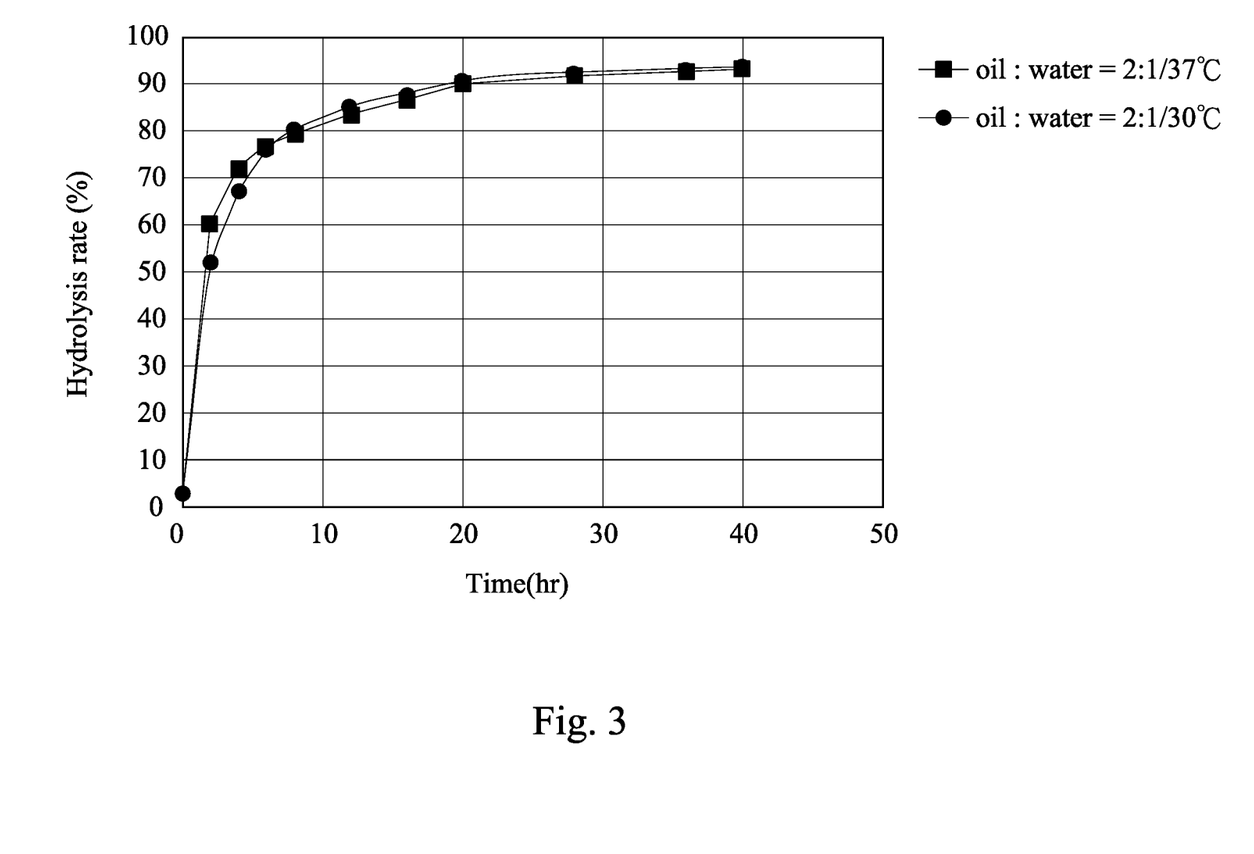
FIG. 3 is a hydrolysis rate relationship diagram of hydrolyzed tallow at different temperatures under the conditions of 2:1 oil-water ratio after emulsification and hydrolysis reactions according to some embodiments of the present disclosure.
Figure 4:
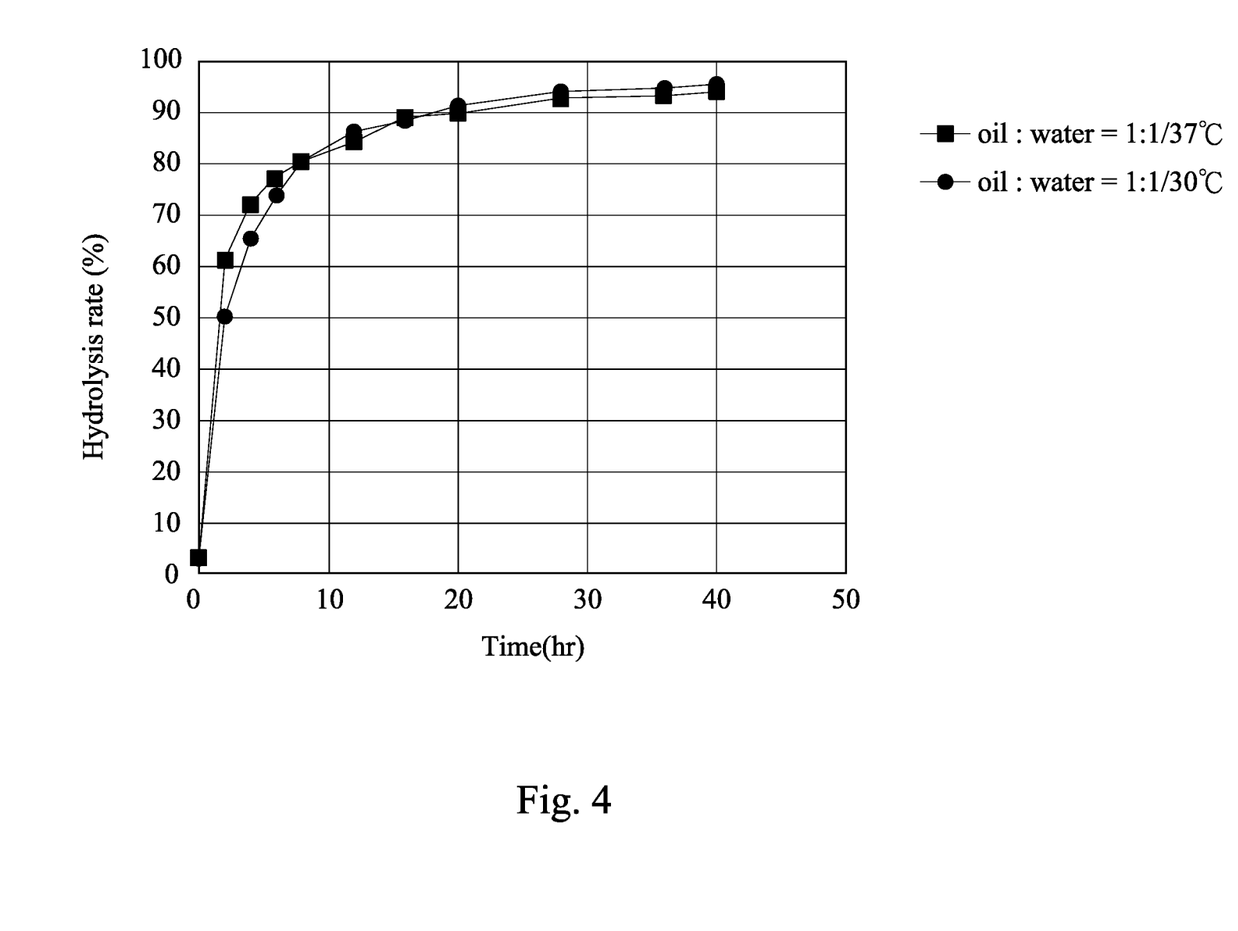
FIG. 4 is a hydrolysis rate relationship diagram of hydrolyzed tallow at different temperatures under the conditions of 1:1 oil-water ratio after emulsification and hydrolysis reactions according to some embodiments of the present disclosure.

FIG. 3 is a hydrolysis rate relationship diagram of hydrolyzed tallow at different temperatures under the conditions of 2:1 oil-water ratio after emulsification and hydrolysis reactions according to some embodiments of the present disclosure. FIG. 4 is a hydrolysis rate relationship diagram of hydrolyzed tallow at different temperatures under the conditions of 1:1 oil-water ratio after emulsification and hydrolysis reactions according to some embodiments of the present disclosure. Referring to FIG. 3 and FIG. 4, the results of example 3 to example 6 were integrated in FIG. 3 and FIG. 4 to compare the hydrolysis rate under different reaction conditions.

Figure 5:
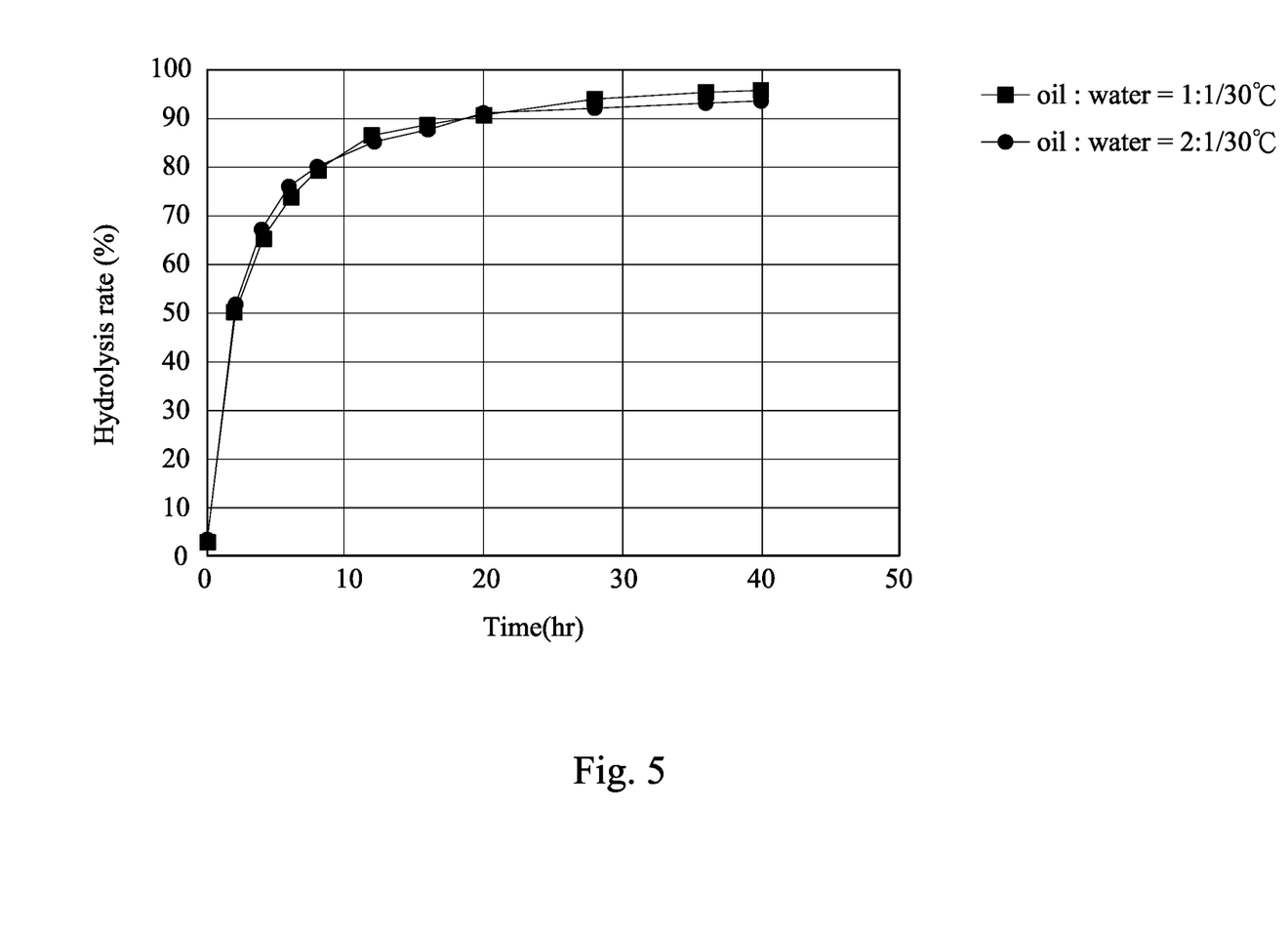
FIG. 5 is a hydrolysis rate relationship diagram of hydrolyzed tallow at 30° C. under and different oil-water ratios after emulsification and hydrolysis reactions according to some embodiments of the present disclosure.

FIG. 5 is a hydrolysis rate relationship diagram of hydrolyzed tallow at 30° C. under different oil-water ratios after emulsification and hydrolysis reactions according to some embodiments of the present disclosure. The results of example 4 and example 6 were integrated in FIG. 5 to compare the hydrolysis rate under different oil-water ratio reaction conditions.

Experimental Example 3 Hydrolysis of Soybean Oil

In this experimental example, under the condition of adding different amounts of rCRL1 (about 6 grams and about 12 grams), an oil-water mixture of 200 grams of crude soybean oil mixed with 100 grams of water was used. The oil-water mixture was stirred and emulsified at 37° C. and a hydrolysis reaction was carried out. The acid value (AV) and the hydrolysis rate (%) in an oil phase layer of the samples were sampled and analyzed at regular period of time. The results are listed in table 3 below.

TABLE 3

| | Example 7 | | Example 8 | |
|---|---|---|---|---|
| | Oil:water (g:g) | | | |
| | 200:100 | | 200:100 | |
| | Amount of rCRL1 (g) | | | |
| | 6 | | 12 | |
| Time (hr) | AV | Hydrolysis rate (%) | AV | Hydrolysis rate (%) |
| 0 | 6.51 | 3.3 | 6.51 | 3.3 |
| 2 | 151.8 | 76.7 | 166.9 | 84.3 |
| 4 | 170.1 | 85.9 | 177.9 | 89.8 |
| 6 | 173.8 | 87.8 | 179.6 | 90.7 |
| 8 | 178.9 | 90.4 | 179.6 | 90.7 |
| 12 | 181.1 | 91.5 | 181.3 | 91.6 |
| 16 | 181.4 | 91.6 | 182.8 | 92.3 |
| 20 | 182.7 | 92.3 | 183.1 | 92.5 |
| 24 | 182.6 | 92.2 | 183.9 | 92.9 |
| 28 | 183.4 | 92.6 | 184.3 | 93.1 |

It can be seen from table 3 that in the case of a fixed oil-water ratio, the higher the concentration of rCRL1, the faster the reaction rate. As for hydrolysis rate, the lower the concentration of rCRL1, the slightly lower the hydrolysis rate.

Figure 6:
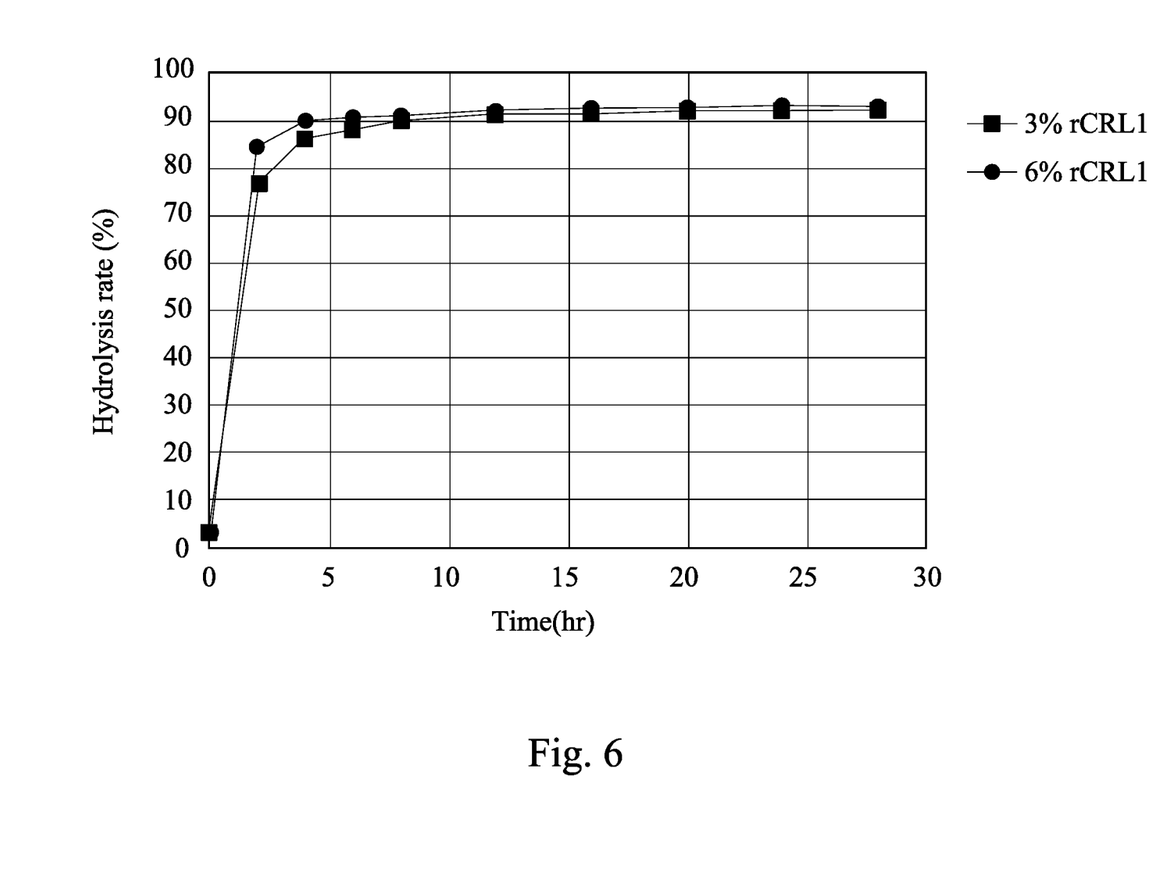
FIG. 6 is a hydrolysis rate relationship diagram of hydrolyzed crude soybean oil at different lipase concentrations after emulsification and hydrolysis reactions according to some embodiments of the present disclosure.

FIG. 6 is a hydrolysis rate relationship diagram of hydrolyzed crude soybean oil at different lipase concentrations after emulsification and hydrolysis reactions according to some embodiments of the present disclosure. The results of example 7 and example 8 were integrated in FIG. 6 to compare the hydrolysis rate under different rCRL1 concentration reaction conditions.

Figure 7:
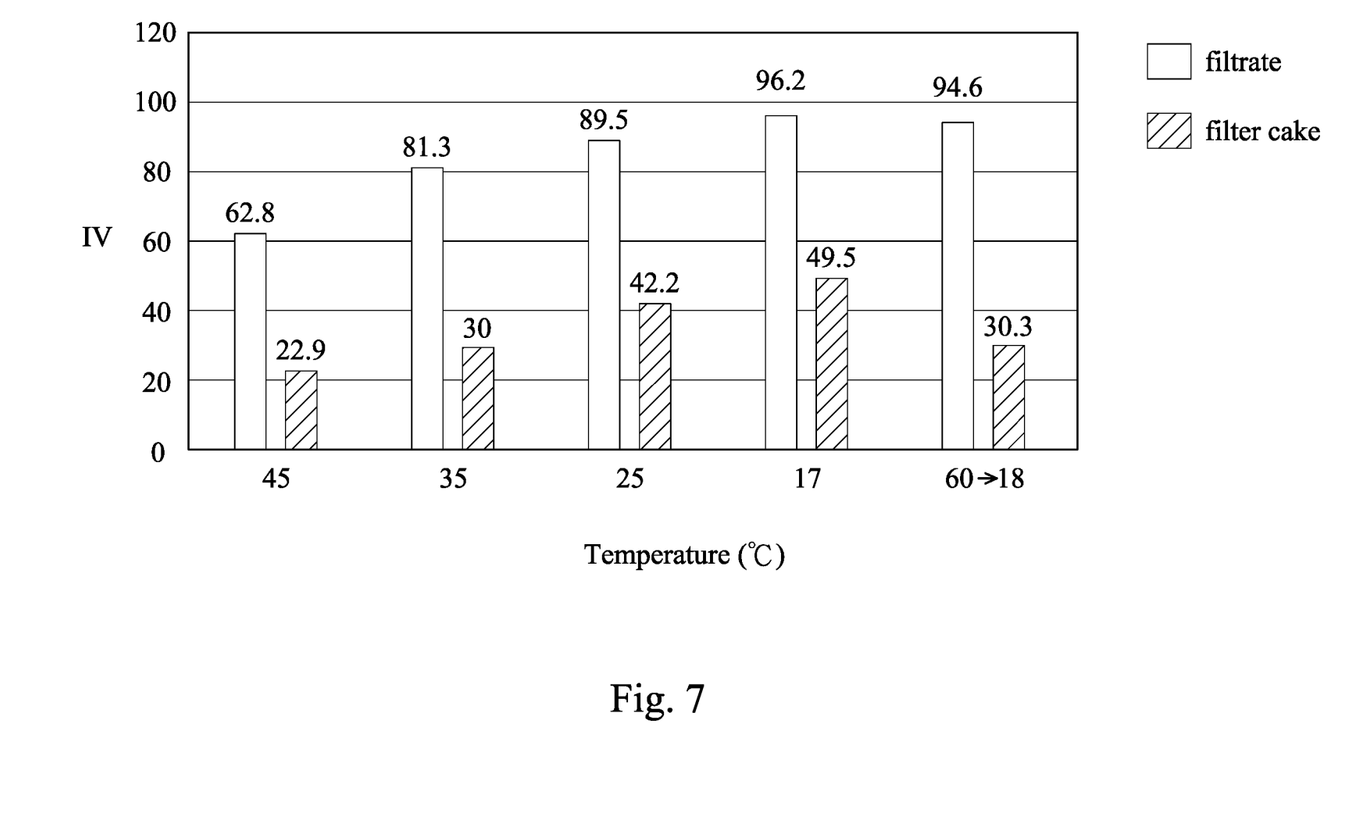
FIG. 7 shows the content of fatty acids of the filtrate and filter cake of filtered crude palm oil hydrolysate according to some embodiments of the present disclosure.
Figure 8:
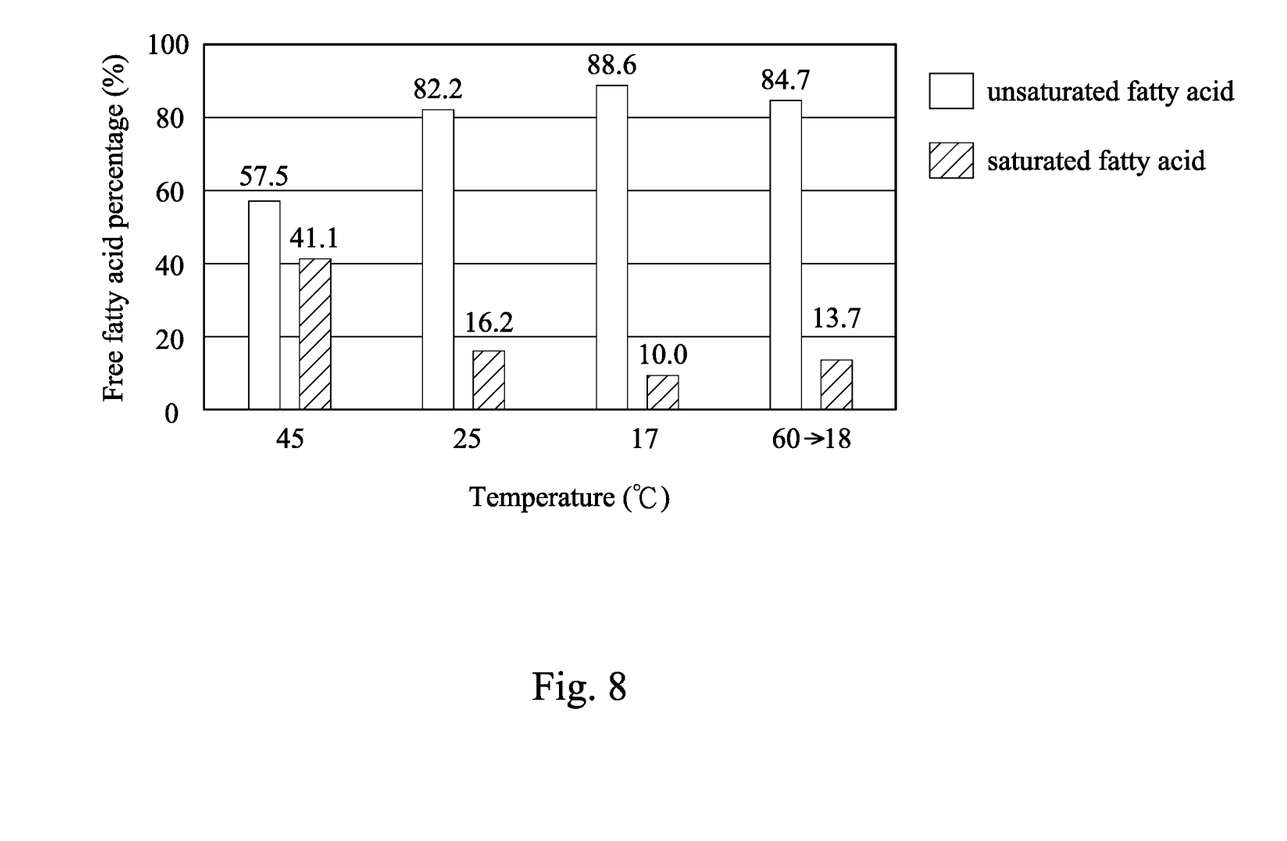
FIG. 8 shows the content of unsaturated fatty acids and saturated fatty acids in the filtrate of filtered crude palm oil hydrolysate according to some embodiments of the present disclosure.

Experimental Example 4 Separation of Saturated Fatty Acids and Unsaturated Fatty Acids from Crude Palm Oil Hydrolysate FIG. 7 shows the content of fatty acids of the filtrate and filter cake of filtered crude palm oil hydrolysate according to some embodiments of the present disclosure. FIG. 8 shows the content of unsaturated fatty acids and saturated fatty acids in the filtrate of filtered crude palm oil hydrolysate according to some embodiments of the present disclosure. Referring to FIG. 7 and FIG. 8, the results of the following two separation experiments were integrated in FIG. 7 and FIG. 8 to compare the iodine value and free fatty acid content under different separation operations.

In one separation experimental example, after the aforementioned example 2 that has been hydrolyzed was allowed to stand at a temperature of about 60° C., the oil phase layer and the water phase layer were separated. Next, about 430 g of the oil phase layer was obtained and then vacuum filtered at about 45° C. was carried out. It is noted that the filtration time of this experimental example was from about 30 minutes to about 1 hour, but not limited thereto. The filtration time varies depending on samples. The obtained filtrate was crystallized by cooling and then vacuum filtered again until the temperature dropped to about 17° C. Each filtered filtrate and filter cake would be sampled and analyzed for iodine value (IV). It can be understood that the higher the iodine value detected, the higher the content of unsaturated fatty acids. As shown in FIG. 7, the IV in the filtrate of each filtration gradually increased from 62.8 to 96.2. In contrast, the IV in the filter cake increased from 22.9 to 49.5. As shown in FIG. 8, the final filtrate contains about 88.6% of unsaturated fatty acids and about 10.0% of saturated fatty acids. Because the operating temperatures of the separation process do not exceed 100° C., the final filtrate mainly contains cis-unsaturated fatty acids.

In another separation experimental example, after the aforementioned example 2 that has been hydrolyzed was allowed to stand at a temperature of about 60° C., the oil phase layer and the water phase layer were separated. Next, about 200 g of the oil phase layer was obtained, slowly cooling and crystallization step was carried out, and then vacuum filtration at about 18° C. was carried out. For example, the slowly cooling step mentioned above is carried out from about 60° C. to about 45° C. in 30 minutes, from about 45° C. to about 35° C. in 30 minutes, from about 35° C. to 25° C. in 30 minutes, and from about 25° C. to about 18° C. in 120 minutes, and the vacuum filtration was then carried out. Next, the IV of the filtrate and the filter cake was sampled and analyzed. As shown in FIG. 7, the IV in the final filtrate was 94.6, and the IV in the final filter cake was 30.3. As shown in FIG. 8, the final filtrate contains about 84.7% of unsaturated fatty acids and about 13.7% of saturated fatty acids. Because the operating temperatures of the separation process do not exceed 100° C., the final filtrate mainly contains cis-unsaturated fatty acids.

Although the present disclosure has been described in considerable detail with reference to certain embodiments thereof, other embodiments are possible. It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A method for producing cis-unsaturated fatty acid by recombinant *Candida rugosa* lipase 1 (rCRL1), the method comprising following operations:
    (i) providing an oil-water mixture, wherein the oil-water mixture comprises 1 to 2 parts by weight of oil and 1 part by weight of water;
    (ii) adding 0.02 to 0.25 parts by weight of a recombinant *Candida rugosa* lipase 1 (rCRL1) into the oil-water mixture;
    (iii) after operation (ii), emulsifying the oil-water mixture without the addition of organic solvents;
    (iv) after operation (iii), hydrolyzing the emulsified oil-water mixture to generate the cis-unsaturated fatty acid;
    (v) after operation (iv), performing an oil-water separation at a temperature of 55° C. to 65° C. and extracting an oil phase layer; and
    (vi) after operation (v), performing a cooling and filtering step to obtain the cis-unsaturated fatty acid.

2. The method of claim 1, wherein the oil comprises a natural woody vegetable oil, a natural herbal oil, a natural animal oil, or a combination thereof.

3. The method of claim 2, wherein the natural woody vegetable oil comprises palm oil, palm kernel oil, olive oil, or camellia oil.

4. The method of claim 2, wherein the natural herbal oil comprises soybean oil, rapeseed oil, peanut oil, sesame oil, or sunflower oil.

5. The method of claim 2, wherein the natural animal oil comprises tallow, lard, or fish oil.

6. The method of claim 1, wherein the operation (iii) is carried out at a temperature from about 25° C. to about 40° C.

7. The method of claim 1, wherein the operation (iv) is carried out at a temperature from about 25° C. to about 40° C.

8. The method of claim 1, wherein the operation (iii) is carried out for about 1-6 hours.

9. The method of claim 1, wherein the operation (iv) is carried out for about 10-40 hours.

10. The method of claim 1, wherein the cooling and filtering step is multiple continuous cooling and filtering steps, the multiple continuous cooling and filtering steps comprises:
- a first cooling and filtering step, wherein a first cooling temperature drops from about 55-65° C. to about 45-48° C.;
- a second cooling and filtering step, wherein a second cooling temperature drops from about 45-48° C. to about 34-37° C.;
- a third cooling and filtering step, wherein a third cooling temperature drops from about 34-37° C. to about 23-27° C.; and
- a fourth cooling and filtering step, wherein a fourth cooling temperature drops from about 23-27° C. to about 16-19° C.

11. The method of claim 1, wherein the cooling and filtering step is a single cooling and filtering step, and a cooling temperature drops from about 55-65° C. to about 16-19° C.

12. The method of claim 1, wherein the oil-water mixture is emulsified by stirring.

13. The method of claim 12, wherein a stirring speed ranges from about 250 rpm to about 500 rpm.

* * * * *